United States Patent
Collins et al.

(10) Patent No.: US 9,789,215 B1
(45) Date of Patent: Oct. 17, 2017

(54) ULTRAVIOLET DISINFECTION SYSTEM

(71) Applicant: RayVio Corporation, Hayward, CA (US)

(72) Inventors: Douglas A. Collins, Hayward, CA (US); Li Zhang, Hayward, CA (US); Yitao Liao, Hayward, CA (US)

(73) Assignee: RayVio Corporation, Hayward, CA (US)

( * ) Notice: Subject to any disclaimer, the term of this patent is extended or adjusted under 35 U.S.C. 154(b) by 0 days.

(21) Appl. No.: 15/094,873

(22) Filed: Apr. 8, 2016

(51) Int. Cl.
*A61L 2/10* (2006.01)
*A61L 9/20* (2006.01)
*C02F 1/32* (2006.01)

(52) U.S. Cl.
CPC ...... *A61L 2/10* (2013.01); *A61L 9/20* (2013.01); *C02F 1/325* (2013.01); *C02F 2201/3222* (2013.01); *C02F 2201/3228* (2013.01); *C02F 2303/04* (2013.01)

(58) Field of Classification Search
CPC ......... H01L 33/32; H01L 33/44; H01L 33/20; H01L 33/24; H01L 33/38; H01L 33/483; H01L 33/486; H01L 33/50; H01L 33/504; H01L 33/508; H01L 33/54; H01L 33/56; H01L 33/60; H01L 33/62; C02F 1/325; C02F 1/008; A61L 2/10; A61L 2/0047; A61L 2/0029; A61L 2/08

USPC ... 250/504 R, 432 R, 453.11, 455.11, 504 H; 210/192, 198
See application file for complete search history.

(56) References Cited

U.S. PATENT DOCUMENTS

| | | | | |
|---|---|---|---|---|
| 7,857,485 | B2* | 12/2010 | Wang | H01L 33/60 257/98 |
| 7,965,036 | B2* | 6/2011 | Yun | C09K 11/584 313/501 |
| 8,884,258 | B1* | 11/2014 | Liao | A61L 2/08 250/504 H |
| 9,455,300 | B1* | 9/2016 | Collins | H01L 27/156 |
| 9,540,252 | B1* | 1/2017 | Collins | C02F 1/325 |
| 2013/0105853 | A1* | 5/2013 | Kneissl | H01L 33/32 257/99 |
| 2016/0089457 | A1* | 3/2016 | Liao | A61L 2/10 250/504 R |
| 2016/0217880 | A1* | 7/2016 | Liao | C02F 1/325 |
| 2016/0271280 | A1* | 9/2016 | Liao | A61L 2/10 |
| 2016/0278424 | A1* | 9/2016 | Liao | A23L 3/28 |
| 2016/0355412 | A1* | 12/2016 | Collins | C02F 1/325 |

* cited by examiner

*Primary Examiner* — David A Vanore

(57) ABSTRACT

Embodiments of the invention include an ultraviolet (UV) source, the UV source including a semiconductor device comprising an active layer disposed between an n-type region and a p-type region. The active layer emits radiation having a peak wavelength in a UV range. A reflector cup is disposed around the UV source. A transparent cover is disposed over the reflector cup.

20 Claims, 2 Drawing Sheets

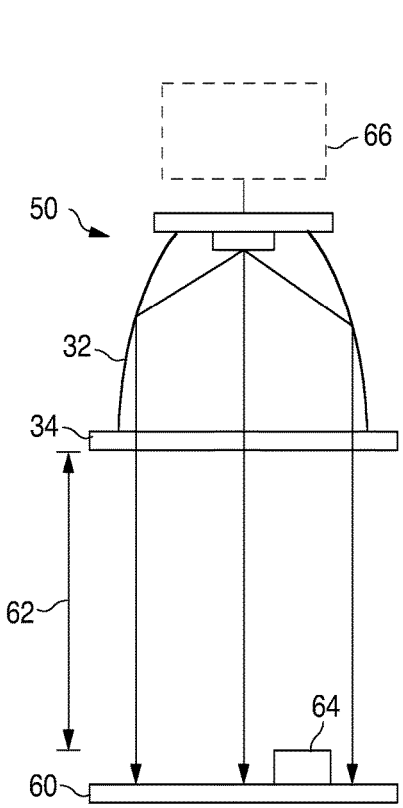
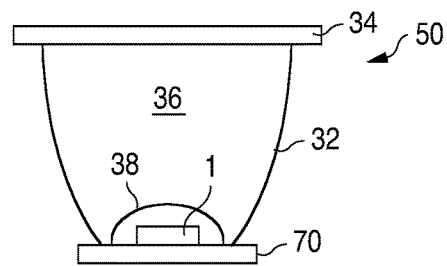
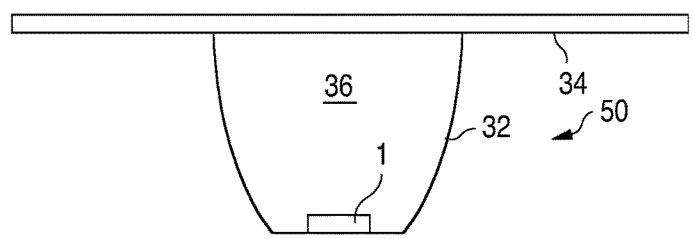
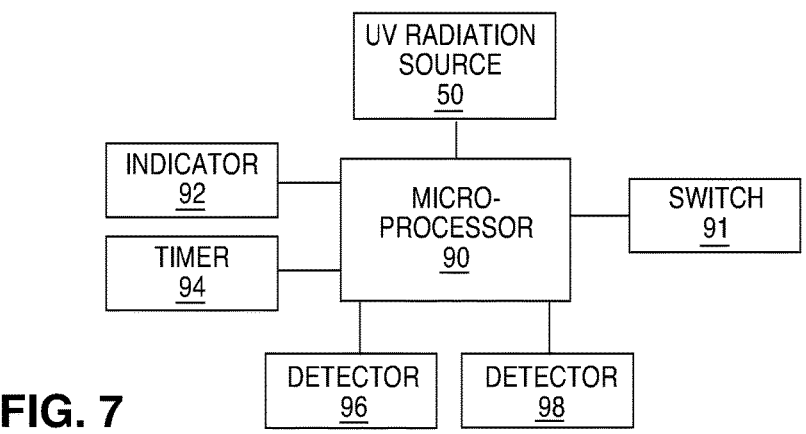
FIG. 4
FIG. 5
FIG. 6
FIG. 7

ULTRAVIOLET DISINFECTION SYSTEM

BACKGROUND

Description of Related Art

The bandgap of III-nitride materials, including (Al, Ga, In)—N and their alloys, extends from the very narrow gap of InN (0.7 eV) to the very wide gap of AlN (6.2 eV), making III-nitride materials highly suitable for optoelectronic applications such as light emitting diodes (LEDs), laser diodes, optical modulators, and detectors over a wide spectral range extending from the near infrared to the deep ultraviolet. Visible light LEDs and lasers can be obtained using InGaN in the active layers, while ultraviolet (UV) LEDs and lasers require the larger bandgap of AlGaN.

UV LEDs with emission wavelengths in the range of 230-350 nm are expected to find a wide range of applications, most of which are based on the interaction between UV radiation and biological material. Typical applications include surface sterilization, water purification, medical devices and biochemistry, light sources for ultra-high density optical recording, white lighting, fluorescence analysis, sensing, and zero-emission automobiles.

UV radiation has disinfection properties that inactivate bacteria, viruses, and other microorganisms. A low-pressure mercury lamp may produce UV radiation in the range of 254 nm. Since most microorganisms are affected by radiation around 260 nm, UV radiation is in the appropriate range for germicidal activity.

BRIEF DESCRIPTION OF THE DRAWINGS

FIG. 4 illustrates a UV radiation source 50, including a UVLED and a lens.

FIG. 5 illustrates the UV radiation source of FIG. 1 used to disinfect an object spaced apart from the UV radiation source.

FIG. 6 illustrates the UV radiation source of FIG. 1 used to disinfect a fluid.

FIG. 7 is a block diagram of a circuit for controlling a UV disinfection system.

DETAILED DESCRIPTION

Though the devices described herein are III-nitride devices, devices formed from other materials such as other III-V materials, II-VI materials, Si are within the scope of embodiments of the invention. The devices described herein may be configured to emit UV A (peak wavelength between 340 and 400 nm), UV B (peak wavelength between 290 and 340 nm), or UV C (peak wavelength between 210 and 290 nm) radiation.

In embodiments of the invention, one or more UVLEDs are used in a packaged UV radiation source. Though any suitable use for the UV radiation source is contemplated in embodiments of the invention, in some embodiments the UV radiation source may be used in a disinfection device, suitable for disinfecting an object, a fluid such as water or air, or any other suitable material or structure.

Figure 1:
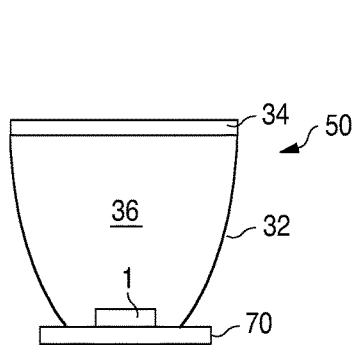
FIG. 1 illustrates a UV radiation source 50, including a UV-emitting device (UVLED).

FIG. 1 illustrates a packaged UV radiation source 50. In the device of FIG. 1, one or more UVLEDs 1 are attached to a mount 70. The mount 70 may be, for example, a ceramic mount, a circuit board, a metal-core printed circuit board, a silicon mount, or any other suitable structure. Circuit elements such as driver circuitry for UVLED 1 or any other suitable circuitry may be disposed on or within mount 70. A single UVLED may be used, multiple UVLEDs disposed in a single package may be used, or multiple packages including one or more UVLEDs each may be used, in order to provide UV radiation sufficient for a given application.

A reflector cup 32 is disposed around UVLED 1. Reflector cup 32 may be any suitable structure. In some embodiments, reflector cup 32 is a hollow structure that is attached, for example, to the mount 70. The inner surfaces of reflector cup 32 are reflective to UV radiation. For example, reflector cup 32 may be fabricated from a reflective material, such as aluminum, formed by any suitable technique including, for example, machining and polishing the reflective surfaces. Alternatively, reflector cup 32 may be fabricated from a non-reflective material that is coated on the inside with a reflective layer. Suitable examples include plastic formed by, for example, molding, injection molding, 3-D printing, or any other suitable technique. Examples of suitable reflective coatings include metals, silver, aluminum, Teflon, polytetrafluoroethylene (PTFE), barium sulfate, oxides, oxides of silicon including $SiO_2$, oxides of yttrium, oxides of hafnium, a multilayer stack, a distributed Bragg reflector, and combinations thereof. The coating may be formed by any suitable technique including, for example, plating, evaporating, or spray coating. The reflective inner surface of reflector cup 32 may have any suitable finish including a mirror finish, a diffusely reflective or "orange peel" finish, or a faceted finish (the facets may have a mirror finish or diffusely reflective finish).

In some embodiments, reflector cup 32 may create a radiation pattern that is more collimated than the radiation pattern emitted by the UVLED 1 without the reflector cup 32. In some embodiments, reflector cup 32 is shaped such that the UV radiation emitted from the device at the top of reflector cup 32 is substantially uniform. In some embodiments, reflector cup 32 may have parabolic sidewalls. The cross section of reflector cup 32, in a plane parallel to a major surface of UVLED 1, may be circular, square, rectangular, oval, or any other suitable shape. Typically reflector cup 32 alters the radiation output pattern by direct reflection, though in some embodiments total internal reflection may be used.

A cover 34 is disposed over the reflector cup 32. The cover may be any material that is resistant to radiation emitted by UVLED 1 and optically transmissive to radiation emitted by UVLED 1. In some embodiments, the cover 34 is transparent to radiation emitted by UVLED 1. Suitable materials include but are not limited to quartz, fused silica, UV-hard plastic films such as Fluorinated ethylene propylene (FEP), silicone, sapphire, UV-transparent glass, and UV-transparent cyclic olefin copolymer (COC) sold under the name TOPAS®. The reflecting cup directs the radiation emitted by UVLED 1 so that it impinges on cover 34 at an angle that is substantially perpendicular to a major surface of cover 34, for example to minimize reflection in some embodiments. In some embodiments, the top side of cover 34 (the side facing away from UVLED 1), the bottom side of cover 34 (the side facing UVLED 1), or both are roughened, textured, or patterned, for example to act as a diffuser to the radiation exiting cover 34.

In some embodiments, the area 36 enclosed by UVLED 1, reflector cup 32, and cover 34 is filled with air or other ambient gas. The area 36 may be sealed, though this is not required in embodiments where the area 36 is filled with ambient gas. In some embodiments, area 36 may be filled with an index-matching material such as lens oil, silicone gel, or a solid material such as quartz or silicone. The index-matching material may be selected to match the index of refraction of UVLED 1 (for example, the growth substrate of UVLED 1, described below), of cover 34, or may be selected to be between the indices of refraction of UVLED 1 and cover 34.

In some embodiments, an optic such as a lens or any other suitable structure is formed or disposed over UVLED 1, as illustrated in FIG. 4. Lens 38 is formed from a material that is transparent to UV radiation at wavelengths emitted by UVLED 1, and able to withstand the UV radiation without degrading. For example, in some embodiments, lens 38 may be formed from a material that transmits at least 85% of UV radiation at 280 nm. The material may degrade no more than 1% after 1000 hrs of exposure to UV radiation at 280 nm. In some embodiments, lens 38 is formed from a material that is moldable, such as, for example, glass, IHU UV transmissive glass available from Isuzu Glass, Inc., and UV-resistant silicone. In some embodiments, lens 38 is formed from a material that may be shaped by, for example, grinding and polishing, such as quartz or sapphire. A lens formed by molding may be less expensive; a lens formed by grinding and polishing may be of better optical quality. A pre-formed lens 38 such as a quartz lens may be is attached to UVLED 1, or disposed over UVLED 1 and attached to mount 70. Lens 38 may be optically coupled to just the top surface of UVLED 1 or to the top and side surfaces of UVLED 1. Lens 38 may be any suitable shape. Though a dome lens is illustrated, other shapes such as Fresnel lenses, hyperbolic lenses, parabolic lenses, and lenses with a square base or a base the same shape as UVLED 1 (i.e. the bottom surface of the lens, and/or the portion of the lens in contact with the top, emission surface of UVLED 1 is square or the same shape as UVLED 1) may be suitable. When a lens 38 is included, area 36 is generally filled with air or other gas, though in some embodiments a liquid, gel, or solid may fill area 36, as described above.

Figure 2:
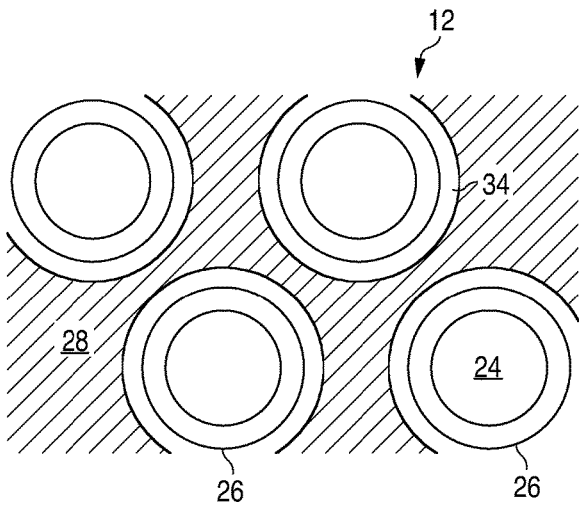
FIG. 2 is a plan view of multiple pixels in a flip chip UVLED.
Figure 3:
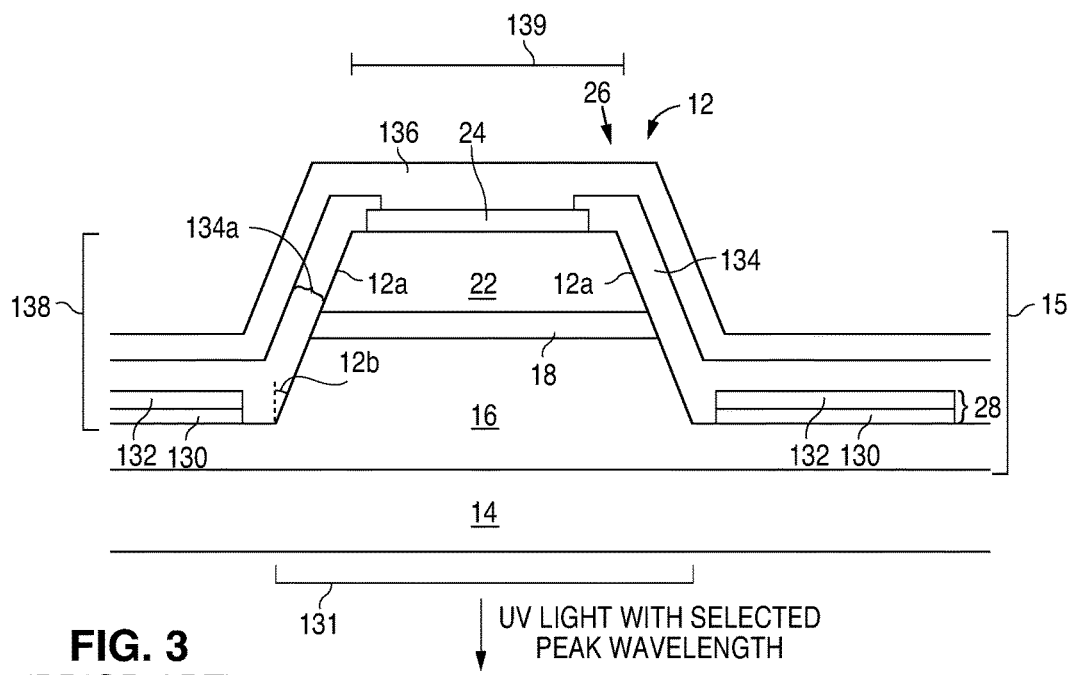
FIG. 3 is a cross sectional view of one pixel in the UVLED of FIG. 2.

Commercially available UVA, UVB, and UVC LEDs may be used in the various embodiments. FIGS. 2 and 3 are examples of the assignee's own UVB and UVC LEDs that may be used. FIG. 2 is a top down view of a portion of an array of UVLED pixels 12, and FIG. 3 is a bisected cross-section of a single UVLED pixel 12. Any suitable UVLED may be used and embodiments of the invention are not limited to the device of FIGS. 2 and 3.

The UVLEDs are typically III-nitride, and commonly GaN, AlGaN, and InGaN. The array of UV emitting pixels 12 is formed on a single substrate 14, such as a transparent sapphire substrate. Other substrates are possible. Although the example shows the pixels 12 being round, they may have any shape, such as square. The light escapes through the transparent substrate, as shown in FIG. 3. The pixels 12 may each be flip-chips, where the anode and cathode electrodes face the mount (described below).

All semiconductor layers are epitaxially grown over the substrate 14. An AlN or other suitable buffer layer (not shown) is grown, followed by an n-type region 16. The n-type region 16 may include multiple layers of different compositions, dopant concentrations, and thicknesses. The n-type region 16 may include at least one $Al_aGa_{1-a}N$ film doped n-type with Si, Ge and/or other suitable n-type dopants. The n-type region 16 may have a thickness from about 100 nm to about 10 microns and is grown directly on the buffer layer(s). The doping level of Si in the n-type region 16 may range from $1\times10^{16}$ cm$^{-3}$ to $1\times10^{21}$ cm$^{-3}$. Depending on the intended emission wavelength, the AlN mole fraction "a" in the formula may vary from 0% for devices emitting at 360 nm to 100% for devices designed to emit at 200 nm.

An active region 18 is grown over the n-type region 16. The active region 18 may include either a single quantum well or multiple quantum wells (MQWs) separated by barrier layers. The quantum well and barrier layers contain $Al_xGa_{1-x}N/Al_yGa_{1-y}N$, wherein $0<x<y<1$, x represents the AlN mole fraction of a quantum well layer, and y represents the AlN mole fraction of a barrier layer. The peak wavelength emitted by a UV LED is generally dependent upon the relative content of Al in the AlGaN quantum well active layer.

A p-type region 22 is grown over the active region 18. Like the n-type region 16, the p-type region 22 may include multiple layers of different compositions, dopant concentrations, and thicknesses. The p-type region 22 includes one or more p-type doped (e.g. Mg-doped) AlGaN layers. The AlN mole fraction can range from 0 to 100%, and the thickness of this layer or multilayer can range from about 2 nm to about 100 nm (single layer) or to about 500 nm (multilayer). A multilayer used in this region can improve lateral conductivity. The Mg doping level may vary from $1\times10^{16}$ cm$^{-3}$ to $1\times10^{21}$ cm$^{-3}$. A Mg-doped GaN contact layer may be grown last in the p-type region 22.

All or some of the semiconductor layers described above may be grown under excess Ga conditions, as described in more detail in US 2014/0103289, which is incorporated herein by reference.

The semiconductor structure 15 is etched to form trenches between the pixels 12 that reveal a surface of the n-type region 16. The sidewalls 12a of the pixels 12 may be vertical or sloped with an acute angle 12b relative to a normal to a major surface of the growth substrate. The height 138 of each pixel 12 may be between 0.1-5 microns. The widths 131 and 139 at the bottom and top of each pixel 12 may be at least 5 microns. Other dimensions may also be used.

Before or after etching the semiconductor structure 15 to form the trenches, a metal p-contact 24 is deposited and patterned on the top of each pixel 12. The p-contact 24 may include one or more metal layers that form an ohmic contact, and one or more metal layers that form a reflector. One example of a suitable p-contact 24 includes a Ni/Ag/Ti multi-layer contact.

An n-contact 28 is deposited and patterned, such that n-contact 28 is disposed on the substantially flat surface of the n-type region 16 between the pixels 12. The n-contact 28 may include a single or multiple metal layers. The n-contact 28 may include, for example, an ohmic n-contact 130 in direct contact with the n-type region 16, and an n-trace metal layer 132 formed over the ohmic n-contact 130. The ohmic n-contact 130 may be, for example, a V/Al/Ti multi-layer contact. The n-trace metal 132 may be, for example, a Ti/Au/Ti multi-layer contact.

The n-contact 28 and the p-contact 24 are electrically isolated by a dielectric layer 134. Dielectric layer 134 may be any suitable material such as, for example, one or more oxides of silicon, and/or one or more nitrides of silicon, formed by any suitable method. Dielectric layer 134 covers n-contact 28. Openings formed in dielectric layer 134 expose p-contact 24.

A p-trace metal 136 is formed over the top surface of the device, and substantially conformally covers the entire top surface. The p-trace metal 136 electrically connects to the p-contact 24 in the openings formed in dielectric layer 134. The p-trace metal 136 is electrically isolated from n-contact 28 by dielectric layer 134.

Robust metal pads electrically connected to the p-trace metal 136 and n-contact 28 are provided outside of the drawing for connection to power supply terminals. Multiple pixels 12 are included in a single UVLED. The pixels are electrically connected by large area p-trace metal 136 and the large area n-trace metal 132. The number of pixels may be selected based on the application and/or desired radiation output. A single UVLED, which includes multiple pixels, is illustrated in the following figures as UVLED 1.

In some embodiments, substrate 14 is sapphire. Substrate 14 may be, for example, on the order of hundreds of microns thick. In a 1 mm square UVLED 1 with a 200 µm thick sapphire substrate, assuming radiation is extracted from the top and sides of the substrate, the top surface accounts for about 55% of the extraction surface, and the sides account for about 45% of the extraction surface of the substrate. Substrate 14 may remain part of the device in some embodiments, and may be removed from the semiconductor structure in some embodiments.

In some embodiments, the top, emission surface of substrate 14 is roughened, patterned, or textured, for example to improve extraction of radiation, or to shape the extraction of radiation from the device. For example, micro-lens arrays, one or more Fresnel lenses, or photonic crystals may be formed in the sapphire substrate. In some embodiments, the opposite, growth surface of the substrate may be roughened, patterned, or textured, for example to facilitate growth and/or to improve extraction of radiation from the semiconductor material into the substrate 14.

The UVLED may be square, rectangular, or any other suitable shape when viewed from the top surface of substrate 14, when the device is flipped relative to the orientation illustrated in FIG. 3.

The UV radiation sources 50 illustrated in FIGS. 1 and 4 may be particularly suited to some disinfection applications. In some embodiments, an object to be disinfected is simply placed on the cover 34. FIGS. 5 and 6 illustrate two disinfection applications using the UV radiation sources illustrated in FIGS. 1 and 4.

In the device of FIG. 5, UV radiation source 50 is spaced apart from an object 64 to be disinfected. The object 64 may be placed on a stage 60. The stage 60 may be placed such that the object 64 is spaced an optimal distance 62 from the output area of the UV radiation source 50 (i.e., the surface of cover 34). The distance 62 may be selected for one or more particular characteristics of the output UV radiation at that point, such as uniformity and/or or radiative power.

In some embodiments, a device 66 for adjusting the distance between the output area of UV radiation source 50 and an object 64 placed on stage 60 is coupled to the UV radiation source 50, the stage 60, or both. The device 66 may include, for example, a sensor for determining the distance between the object and the UV radiation source, and a motor for moving one of the UV radiation source 50 and the stage 60 up or down, such that the distance between the object and the UV radiation source is the optimal distance 62 for disinfection.

In some embodiments, the stage 60 may be configured to move the object 64 past the output area of the UV radiation source 50. For example, the stage 60 may be a conveyor belt. One application of the system illustrated in FIG. 5 is a conveyor belt on which a user places a cell phone, laptop, or other object, such that the object passes under the UV power emitted from the output surface of UV radiation source 50 and is disinfected.

In the device of FIG. 6, the UV radiation source is coupled to a chamber containing liquid or gas to be disinfected. The cover 34 may form a wall of the chamber, as illustrated, or the cover may be optically coupled to a separate wall of the chamber.

FIG. 7 is a block diagram of a circuit, which may control a UV radiation source in any suitable application such as, for example, the disinfection applications described above. The number of UV radiation sources 50 and the time needed for disinfection may be easily calculated as is known in the art. Any suitable circuit may be used. Not all of the components illustrated in FIG. 7 are necessary in all embodiments. The components may be disposed on or in a mount, described above, and electrically connected to each other as illustrated via the mount, a circuit board, or any other suitable structure. UV radiation source 50 may be connected to a microprocessor 90, which may turn the UV radiation source 50 on and off, and may adjust the power to UV radiation source 50. A switch 91, which may be user-activated or automatic, and may be any suitable switch, may activate the UV radiation source directly (not shown in FIG. 7), or may activate the microprocessor, which turns on the UV radiation source.

The amount of time that a fluid or object is exposed to radiation from UV radiation source may be dictated by a timer 94, which may count a predetermined amount of time, after which the microprocessor 90 may turn off UV radiation source 50. An indicator 92, such as a light or any other suitable indicator, may indicate whether UV radiation source 50 is emitting UV radiation.

A detector 96 may detect an amount of UV radiation at a given point in the disinfection system. The amount of UV radiation emitted by source 50 may be adjusted accordingly by microprocessor 90. A second detector 98 may be used to detect whether the UV radiation source 50 is functioning properly. For example, first detector 96 may be positioned near UV radiation source 50, and second detector 98 may be positioned far from UV radiation source 50. When UV radiation source 50 is on, the amount of UV radiation detected by each of detectors 96 and 98 may be compared. If detector 96 indicates a higher amount of UV radiation and detector 98 indicates a lower amount of UV radiation, a fluid may be contaminated with particulate matter. If detectors 96 and 98 both indicate a low amount of UV radiation, the UV radiation source 50 may not be functioning properly. Indicator 92 may be used to indicate to a user that UV radiation source 50 is not functioning properly.

In one operation, a user activates switch 91. In response, microprocessor 90 turns on UV radiation source 50. Microprocessor 90 may also switch indicator 92 to a status indicating the UV radiation source is disinfecting. The amount of UV radiation is measured by detector 96. In response, microprocessor 90 may adjust the amount of time that the UV radiation source 50 stays on, and/or the power to UV radiation source 50, in order to deliver a sufficient dose of UV radiation to disinfect the fluid. Once the dose is reached, microprocessor 92 may switch off UV radiation source 50, and switch off indicator 92 or change indicator 92 to a status indicating the UV radiation source is finished disinfecting.

Having described the invention in detail, those skilled in the art will appreciate that, given the present disclosure, modifications may be made to the invention without departing from the spirit of the inventive concept described herein.

In particular, different features and components of the different devices described herein may be used in any of the other devices, or features and components may be omitted from any of the devices. A characteristic of, for example, the optic, described in the context of one embodiment, may be applicable to any embodiment. Suitable materials described for a particular component in a particular embodiment may be used for other components, and/or in other embodiments. Therefore, it is not intended that the scope of the invention be limited to the specific embodiments illustrated and described.

What is being claimed is:

1. A structure comprising:
   an ultraviolet (UV) source comprising a semiconductor device comprising an active layer disposed between an n-type region and a p-type region, wherein the active layer emits radiation having a peak wavelength in a UV range;
   a reflector cup disposed around the UV source, a surface of the reflector cup facing the UV source comprising a direct, diffuse reflector; and
   an optically transmissive cover disposed over the reflector cup.

2. The structure of claim 1 further comprising a liquid, gel, or solid material disposed between the UV source and the optically transmissive cover.

3. The structure of claim 2 wherein the UV source comprises a growth substrate, and an index of refraction of the material is between an index of refraction of the optically transmissive cover and an index of refraction of the growth substrate.

4. A structure comprising:
   an ultraviolet (UV) source comprising a semiconductor device comprising an active layer disposed between an n-type region and a p-type region, wherein the active layer emits radiation having a peak wavelength in a UV range;
   a reflector cup disposed around the UV source; and
   an optically transmissive cover disposed over the reflector cup, wherein the optically transmissive cover is oriented to form a stage on which an object to be disinfected is placed.

5. The structure of claim 4 further comprising a liquid, gel, or solid material disposed between the UV source and the optically transmissive cover.

6. The structure of claim 4 wherein a major surface of the optically transmissive cover is roughened.

7. The structure of claim 4 further comprising an optic disposed over the UV source.

8. The structure of claim 1 further comprising an optic disposed over the UV source.

9. The structure of claim 1 wherein the optically transmissive cover is oriented to form a stage on which an object to be disinfected is placed.

10. The structure of claim 1 wherein the optically transmissive cover forms a sidewall of a vessel suitable for containing a fluid.

11. The structure of claim 1 wherein a major surface of the optically transmissive cover is roughened.

12. A structure comprising:
    an ultraviolet (UV) source comprising a semiconductor device comprising an active layer disposed between an n-type region and a p-type region, wherein the active layer emits radiation having a peak wavelength in a UV range;
    a reflector cup disposed around the UV source; and
    an optically transmissive cover disposed over the reflector cup, wherein the optically transmissive cover forms a sidewall of a vessel suitable for containing a fluid.

13. The structure of claim 12 further comprising a liquid, gel, or solid material disposed between the UV source and the optically transmissive cover.

14. The structure of claim 12 further comprising an optic disposed over the UV source.

15. The structure of claim 12 wherein a major surface of the optically transmissive cover is roughened.

16. A structure comprising:
    an ultraviolet (UV) source comprising a semiconductor device comprising an active layer disposed between an n-type region and a p-type region, wherein the active layer emits radiation having a peak wavelength in a UV range;
    a reflector cup disposed around the UV source; and
    an optically transmissive cover disposed over the reflector cup, wherein the optically transmissive cover is optically coupled to a sidewall of a vessel suitable for containing a fluid.

17. The structure of claim 16 further comprising an optic disposed over the UV source.

18. A structure comprising:
    an ultraviolet (UV) source comprising a semiconductor device comprising an active layer disposed between an n-type region and a p-type region, wherein the active layer emits radiation having a peak wavelength in a UV range;
    a reflector cup disposed around the UV source; and
    an optically transmissive cover disposed over the reflector cup, wherein a major surface of the optically transmissive cover is roughened.

19. The structure of claim 18 further comprising a liquid, gel, or solid material disposed between the UV source and the optically transmissive cover.

20. The structure of claim 18 further comprising an optic disposed over the UV source.

* * * * *